United States Patent [19]

Clausen et al.

[11] Patent Number: 4,960,955
[45] Date of Patent: Oct. 2, 1990

[54] PROCESS FOR MAKING 4-CHLORO-2-METHYL-5-NITRO-PHENOL

[75] Inventors: Thomas Clausen, Alsbach; David Rose, Hilden, both of Fed. Rep. of Germany

[73] Assignee: Wella Aktiengesellschaft, Darmstadt, Fed. Rep. of Germany

[21] Appl. No.: 353,799

[22] Filed: May 17, 1989

[30] Foreign Application Priority Data

May 18, 1988 [DE] Fed. Rep. of Germany ....... 3816839

[51] Int. Cl.$^5$ ............................................. C07C 79/32
[52] U.S. Cl. ..................... 568/709; 568/706; 568/713
[58] Field of Search .................. 568/709, 713, 706

[56] References Cited

U.S. PATENT DOCUMENTS

| | | | |
|---|---|---|---|
| 3,312,599 | 4/1967 | Koshland, Jr. et al. | 568/709 |
| 3,903,178 | 9/1975 | Nakamura et al. | 568/709 |
| 4,038,328 | 7/1977 | Pelster | 568/709 |

FOREIGN PATENT DOCUMENTS 1057536  3/1986  Japan ................................... 568/709

*Primary Examiner*—Werren B. Lone
*Attorney, Agent, or Firm*—Michael J. Striker

[57] ABSTRACT

The process of making 4-chloro-2-methyl-5-nitro phenol (I)

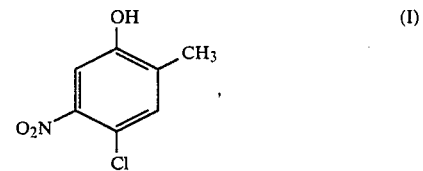

comprises nitrating a 4-chloro-2-methyl-phenyl sulfonate of the formula (II) at the 5 position

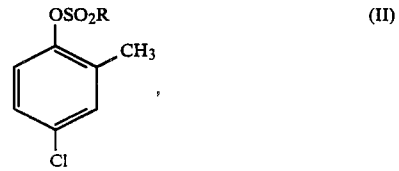

in which R is a residue selected from the group consisting of methyl-, ethyl-, trifluoromethyl-, phenyl- and tolyl and the sulfonyl residue comprises —SO$_2$R at the position 5 to form 4-chloro-2-methyl-5-nitro-phenyl-sulfonate and then cleaving the sulfonyl residue of the 4-chloro-2-methyl-5-nitro-phenyl-sulfonate to form the 4-chloro-2-methyl-5-nitro-phenyl. The process uses technically available and economical starting materials and allows an isomerically pure product to be made in very good yield.

13 Claims, No Drawings

PROCESS FOR MAKING 4-CHLORO-2-METHYL-5-NITRO-PHENOL

BACKGROUND OF THE INVENTION

My invention relates to a process for making coupling agents for oxidizing hair dye compositions and, more particularly, to a process for making 4-chloro-2-methyl-5-nitro-phenol.

The derivatives of m-aminophenol have great significance as coupling agents for the red range for use in oxidizing hair dye compositions. Recently new m-aminophenol derivatives have been made which are characterized by a high light fastness and good toxicological properties. This kind of m-aminophenol derivative is described for example in the German Open Patent Application No. 3 524 329. The final preliminary stage compound or primer for making of all compositions named in that application is 4-chloro-2-methyl-5-nitro-phenol of the formula(I):

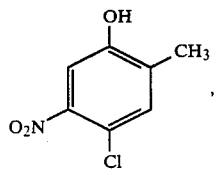

whose manufacture is known from British Patent No. 1 100 219.

The process described there is based on 4-chloro-2-methyl aniline, which is first nitrated and subsequently is converted into the nitrophenol (I) by diazotizing and cooking. More recently it has been found that 4-chloro-2-methyl-aniline can produce bladder cancer. Thus the above-described manufacturing process can no longer be used for the amounts required in the typical chemical engineering process.

The nitration of technically available and very economical 4-chloro-2-methyl-phenol is described in the Literature(Zincke, Liebigs Ann. Chem., Seite 417, 222. That transformation results however in a 4-chloro-2-methyl-6-nitro-phenol which is an isomer of the compound (I).

Another process for making 4-chloro-2-methyl-5-nitro-phenol is described in French Patent No. 2 106 907. There the bis-carbonic acid ester of 4-chloro-2-methyl-phenol is first nitrated and subsequently cleaved by alkaline hydrolysis. Among the disadvantages of this process is the required production of bis-carbonic acid ester, which occurs with phosgene or its derivatives and thus produces a safety problem. Also the yield on nitration is poor. The isomeric product called for by the drastic product conditions requires an additional purification step, after whose performance a yield of only 57% of the theoretical yield is attained.

SUMMARY OF THE INVENTION

Accordingly, it is an object of my invention to provide a manufacturing process for making 4-Chloro-2-methyl-5-nitro-phenol(I) which produces an isomerically pure product in high yield with commercially available economical starting materials.

According to our invention 4-Chloro-2-methyl-5-nitro-phenol(I) can be made without difficulty and with very good yield from 4-Chloro-2-methyl-phenol, when the hydroxyl group of the starting material is protected with a sulfonyl residue, the intermediate product arising is nitrated and subsequently the sulfonyl residue is cleaved.

In keeping with the above object and with others which will become apparent hereinafter our process of making 4-Chloro-2-methyl-5-nitro-phenol (I)

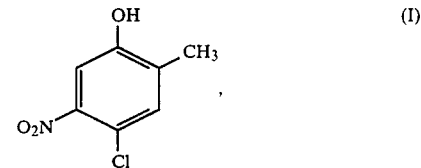

comprises nitrating at the 5-position

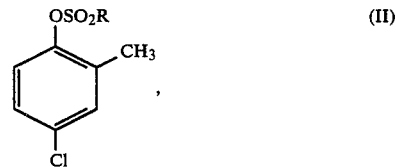

in which R is the residue or functional group methyl-, ethyl-, trifluoromethyl-, phenyl- or tolyl-, and $SO_2R$ comprises a sulfonyl residue and then cleaving the resultant intermediate product, 4-chloro-2-methyl-5-nitro-phenyl-sulfonate to form the product of the formula (I). Advantageously either acid or alkaline cleavage may be used.

The special value of the process is based on the use of temporarily-bound sulfonyl residues which direct the entering nitro group to the 5-position so that very economical starting materials can be used with 4-Chloro-2-methyl-phenol. The nitration occurs under conditions in which the sulfonyl residues can not be attacked during the reaction.

Compounds of the formula(II) are known either in the case of R=phenyl or tolyl(e.g. British Patent No. 984 305; A. R. Parikh et al., J.Inst.Chemists(India), Vol.XLV, May 1973, p.91). Other compounds having the formula (II) may be made in an analogous way according to the process described for R=methyl and phenyl.

Although the process according to our invention can be performed with a wide variety of sulfonate protective groups described in the literature, e.g. with T. W. Greene, Protective Groups in Organic Chemistry, Wiley Interscience, New York(1981), the methane, ethane, trifluoromethane, benzene or tolyl sulfonate are particularly suitable.

The process according to our invention in which the compound of the formula (II) is the 4-Chloro-2-methyl-phenyl-methane-sulfonate, is particularly advantageous. The 4-Chloro-2-methyl-phenyl-methane-sulfonate is made by reaction of 4-Chloro-2-methyl-phenol with methane sulfonyl chloride in the presence of pyridine. The product of this reaction is isolated by addition of ice and subsequent extraction with ether. Subsequently the 4-Chloro-2-methyl-phenyl-methane-sulfonate is nitrated with a mixture of sulfuric acid and nitric acid at about 0° C. Subsequently the cleavage of the methane sulfonyl residue occurs either by acidic ester cleavage, e.g. by heating of 4-Chloro-2-methyl-5-nitro phenyl-methane-sulfonate in concentrated hydrochloric acid at a temperature of about 80° C., or by alkaline ester cleavage, e.g. by reaction of 4-Chloro-2-methyl-5-nitro-phenyl-methane-sulfonate with sodium methylate or methanolic calcium hydroxide solution at room temperature, whereby the desired product 4-Chloro-2-methyl-5-nitro-phenol (I) occurs pure and in good yield.

In one embodiment of the process of our invention which is particularly suitable for manufacture of 4-Chloro-2-methyl-5-nitro-phenol(I) in commercial quantities the intermediate compound comprises 4-Chloro-2-methyl-5-nitro-phenyl-benzene-sulfonate. The making of the 4-Chloro-2-methyl-phenyl-benzene sulfonate occurs by reaction of 4-Chloro-methyl-phenol with benzene-sulfonyl-chloride. This reaction is described in British Patent No. 984 305 and the publication, Le Van Thoi et al, Ann.Fac.Sci.Univ. Saigon 1962, pp. 73–88; CA 62, 2730b. While in the first case pyridine acts as base and solvent, in the second case acetone acts as solvent and alkali hydroxide acts as base. In both cases an additional step is necessary for the isolation of product from the solution.

It has been found that 4-Chloro-2-methyl-phenyl-benzene-sulfonate is obtained directly in its crystalline form, when an aqueous sodium hydroxide solution is added dropwise to a mixture of 4-chloro-2-methyl-phenol and benzene sulfonyl chloride heated to a temperature of about 60° to 70° C.

The nitration of 4-Chloro-2-methyl-phenyl-benzene sulfonate can occur in a process according to our invention already at about 15° C. without side reactions or by-products arising. Advantageously the nitration occurs at about 15° to 17° C. That leads to the 4-Chloro-2-methyl-5-nitro-phenyl-benzene-sulfonate, which may be easily purified by recrystallization.

The cleavage of the benzene sulfonyl residue is performed with aqueous sodium hydroxide solution at reflux temperature The desired product, 4-Chloro-2-methyl-5-nitro-phenol (I) is obtained with high purity and in very good yield.

The following examples illustrate our invention in detail, however; the scope of the invention as set forth in the following claims should not be construed as being limited by the details of these examples.

EXAMPLES

Example A: Making of (I) using the Methane Sulfonyl Protective Group

Step 1: 4-Chloro-2-methyl-phenyl-methane-sulfonate 90.0 g(0.63 mol) 4-Chloro-2-methyl-phenol are mixed with 81 ml( 1.0 mol) pyridine. One adds 57 ml (0.75 mol) of methane sulfonyl chloride dropwise with stirring so that the temperature does not exceed 80° C. The starting material is heated for 2 hours at 80° C. after dropwise addition. Subsequently the starting material is poured into ice, the mixture extracted with ether and the combined ether phases are washed with 2 N hydrochloric acid and neutral water. After drying the ether phase the sulfonic acid ester remains as an almost colorless aqueous mass, which can be used in step 2 without purification. The yield amounts to about 129.1 g( 94 % of the theory). A purification of the aqueous mass by filtration with suction with washing by methanol leads to colorless crystalline needles, which melt after drying at 34°–35° C.

Step 2: 4-Chloro-2-methyl-5-nitro-phenyl-methane-sulfonate 20.0 g(91 ml) of sulfonic acid ester from step 1 is added dropwise to 100 ml(1877 mmol) of concentrated sulfuric acid with cooling and stirring. Subsequently 6 ml(133 mmol) of concentrated nitric acid are added dropwise at −5° to 0° C. The starting material is stirred at 0° C. for about 130 minutes and subsequently poured into ice. Then the precipitated crystals are washed with water and isolated by filtration with suction. After drying one obtains 22.9 g(95% theoretical yield) of the nitro compound with a melting point of 97° to 99° C. The use of the crystalline esters from step 1 as starting materials produces an isomerically pure 4-Chloro-2-methyl-5-nitro-phenyl-methane-sulfonate with a melting point of 99° C.

Step 3: 4-Chloro-2-methyl-5-nitro-phenol(I)

Alkaline Ester Cleavage (a) 5.0 g(19 mmol) of the ester from step 2 are dissolved in a solution of 4.2 g (778 mol) sodium methylate in 100 ml methanol. The principal part of the solution is evaporated in vacuum at room temperature after one hour of stirring. After neutralization with 2 N hydrochloric acid one obtains 3.5 g (99% of the theoretical yield) of the pure phenol derivative(I) with a melting point of 134° C.

(b) 13.25 g (50 mmol) of the ester from step 2 are slurried in 50 ml of methanol and a portion of the ester is dissolved. 20 ml of a 20% methanolic calcium hydroxide solution is added at room temperature. The mixture is heated to 36° C., turns an orange color and simultaneously produces a precipitate. After about one hour stirring one pours the reaction mixture into 400 ml of water and acidifies with acetic acid. The pure phenol(I) precipitates and is filtered with suction. The yield amounts to 7.7 g(83% of the theoretical yield).

Acid Ester Cleavage (c) 4.3 g (16 mmol) of the Ester from Step 2 are heated over night in 20 ml of concentrated hydrochloric acid at about 80° C. After cooling the phenol derivative, which is isolated by vacuum filtration and washing with water, is crystallized out. After drying one obtains 2.2 g (73% of the theoretical yield) of the pure phenol derivative (I).

Example B: Making of (I) using the Benzene Sulfonic Acid Protective Group

Step 1: 4-Chloro-2-methyl-phenyl-benzene-sulfonate

A mixture of 114.1 g (0.8 mol) 4-Chloro-2-methyl-phenol and 141.3 g (0.8 mol) Benzene sulfonic acid chloride is heated at 60° to 70° C. One adds a solution of 32 g (0.8 mol) sodium hydroxide in 1.1 l water dropwise in a time interval of about 30 minutes and subsequently stirs the mixture for about 2 hours at 60° C. After that the mixture is cooled and the precipitate is filtered with suction. The yield amounts to 202.1 g (89.3% of the theoretical yield). The product can be used without purification in step 2.

Step 2: 4-Chloro-2-methyl-5-nitro-phenyl-benzene sulfonate 113 g (0.4 mol) of the sulfonic acid ester from step 1 are fed to 450 ml of concentrated sulfuric acid at room temperature under powered stirring. Subsequently 41 g (0.42 mol) concentrated nitric acid are added dropwise at 15° to 17° C. in a time interval of 3 hours. After 2 hour's time stirring at 15° C. the mixture is poured into ice and the precipitated crystals are filtered by suction.

After washing with water the crystals are dried in vacuum at 50° C. The yield amounts to about 122.3 g. The product is recrystallized from ethanol. The yellow crystal needles obtained after recrystallization have a melting point of 99° to 105° C. The previously described reaction can also be performed with half the amount of sulfuric acid.

Step 3: 4-Chloro-2-methyl-5-nitro-phenol 84.2 (0.26 mol) of the ester from step 2 are suspended in 1 l of water and mixed with 30.8 g (0.77 mol) of sodium hydroxide platelets. After 2 hours cooking under reflux the starting material is cooled and the solution is adjusted to a pH value of 2.1 with 2 N hydrochloric acid. The precipitated material is filtered by suction, washed with water and dried in vacuum at 50° C. The yield amounts to about 45.6 g 95.4% of the theoretical yield).

By "at the 5 position" in the following claims we mean at a particular carbon atom on the benzene ring, i.e. the fifth carbon atom of the ring when the carbon atoms are number sequentially from one to six in a clockwise direction starting with the carbon to which the hydroxyl group (in the phenol) or the sulfonyl group is attached.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of this invention.

What is claimed as new and desired to be protected by Letters Patent is set forth in the appended claims.

What is claimed is:

1. A process of making 4-Chloro-2-methyl-5-nitro-phenol (I)

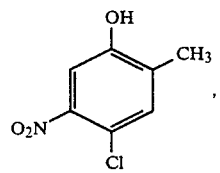

comprising nitrating with a mixture of nitric acid and sulfuric acid a 4-chloro-2-methyl-phenyl-sulfonate of the formula (II) at the 5 position

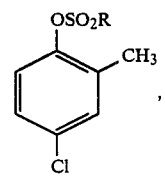

in which R is a residue selected from the group consisting of methyl-, ethyl-, trifluoromethyl-, phenyl- and tolyl- and SO₂R includes a sulfonyl residue, to form 4-Chloro-2-methyl-5-nitro-phenyl sulfonate and then cleaving said sulfonyl residue of said 4-chloro-2-methyl-5-nitro-phenyl sulfonate in the presence of a member selected from the group consisting of an acid and an alkali to form said 4-chloro-2-methyl-5-nitro-phenol.

2. The process according to claim 1 in which said cleaving is performed by acid cleavage.

3. The process according to claim 1 in which said cleaving is performed by alkaline cleavage.

4. The process according to claim 1 in which said 4-chloro-2-methyl-phenyl-sulfonate comprises 4-chloro-2-methyl-phenyl-methane-sulfonate.

5. The process according to claim 4 further comprising making said 4-chloro-2-methyl-phenyl-methane-sulfonate by reaction of 4-Chloro-2-methyl-phenol with methane sulfonyl chloride in the presence of pyridine.

6. The process according to claim 1 in which said cleaving of said sulfonyl residue occurs in concentrated hydrochloric acid.

7. The process according to claim 1 in which said cleaving of said sulfonyl residue occurs with sodium methylate.

8. The process according to claim 1 in which said cleaving of said sulfonyl residue occurs with methanolic calcium hydroxide.

9. The process according to claim 1 in which said 4-chloro-2-methyl-phenyl-sulfonate comprises 4-chloro-2-methyl-phenyl-benzene-sulfonate.

10. The process according to claim 9 further comprising making said 4-chloro-2-methyl-phenyl-benzene-sulfonate by reaction of 4-Chloro-2-methyl-phenol with benzene sulfonyl chloride in the presence of an aqueous solution of sodium hydroxide.

11. The process according to claim 10 in which said reaction of 4-chloro-2-methyl-phenol with said benzene sulfonyl chloride proceeds at from 60° to 70° C.

12. The process according to claim 9 in which said nitrating occurs at 15° to 17° C.

13. The process according to claim 9 in which said cleaving of said cleavage of said benzene sulfonyl residue occurs with aqueous sodium hydroxide.

* * * * *